United States Patent [19]

Benardella

[11] Patent Number: Plant 6,508

[45] Date of Patent: Jan. 3, 1989

[54] ROSE PLANT NAMED BENAROS

[75] Inventor: Frank A. Benardella, Old Tappen, N.J.

[73] Assignee: Nor'East Miniature Roses, Inc., Rowley, Mass.

[21] Appl. No.: 30,430

[22] Filed: Mar. 26, 1987

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new unusual pink and cream blend miniature rose variety.

1 Drawing Sheet

The present invention relates to a new and distinct variety of rose plant of the miniature rose class, which was originated by my crossing as seed parent the rose known as "Rise 'N Shine" (U.S. Plant Pat. No. 4,231) and as pollen parent an unnamed, unpatented seedling of my creation. The denomination of this new rose is "Benaros".

Among the novel characteristics possessed by this new variety which distinguish it from its parents and all other varieties of which I am aware are its unusual pink and cream blend flowers of excellent exhibition hybrid tea-like form and which are long lasting on the plant and after cutting. Asexual reproduction by budding of the new variety as performed in Essex County, Mass. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "4D" is plate 4D of The Royal Horticultural Society Colour Chart.

Parentage: Seedling.

*Seed parent.*—"Rise 'N Shine".

*Pollen parent.*—Unnamed seedling.

Class: Miniature.

The following observations are made of specimens grown outdoors in Essex County, Mass., during the month of September.

FLOWER

Blooming habit: Continuous.

A. Bud:

(1) *Size.*—Medium.

(2) *Form.*—Pointed.

(3) *Color.*—As sepals separate, bud color is mainly Primrose Yellow, near 4D, with some deep pink staining and at petal edge.

(4) *Sepals.*—Foliated, much longer than bud.

(5) *Peduncle.*—Length — about 1 inch. Aspect — straight. Strength — erect. Color — near 146C.

B. Bloom:

(1) *Size.*—Average size when fully expanded — about 1¼ inches.

(2) *Borne.*—Singly, one to a stem and several together in sprays.

(3) *Form.*—High centered, pointed bud. Flowers also high centered at first becoming flat. Outer petals reflex and quill to points; inner petals roll under. Spiral arrangement of petals remains distinct.

(4) *Petalage.*—Number of petals under normal conditions — about 30–33.

(5) *Color.*—After sepals fall and petals unfurl, flowers are well formed exhibition style and of yellow blend coloring. Coloring of petal top surface, visible as flower opens, is not distinct because of mixed blending of yellow and pink tones and color washing but petal edge is typically deep pink or light red varying in intensity from near Rose Bengal, 57C, to Rhodamine Pink, 62A, through 62D. This pink coloring is also visible as petal veining, sometimes appearing also as a speckling on a pale yellow background. Yellow tonality appears deeper on inside of flower, notably on petal undersurface as it becomes visible and also at lower portions of petal top surface extending toward petal base. General tonality from a distance is a pink and cream blend.

C. Petals:

(1) *Texture.*—Thick.

(2) *Appearance.*—Inside velvety and outside satiny.

(3) *Form.*—Broad, fan shaped.

(4) *Arrangement.*—Regularly arranged.

(5) *Petaloids in center.*—Few.

(6) *Persistence.*—Drop off cleanly.

(7) *Fragrance.*—Slight.

(8) *Lasting quality.*—Very long lasting quality on plant and as cut flower.

REPRODUCTIVE ORGANS

A. Stamens, filaments and anthers:

*Arrangement and color.*—Regularly arranged around styles. Color — filaments near 22B.

B. Pollen:

*Color.*—Near 22A.

C. Styles: Medium, thin.

D. Stigmas:

Color.—Near 160C.

E. Hips: None observed.

PLANT

A. Form: Compact.

B. Growth: Very vigorous, uniform branching.
*Height attained.*—About 14–16 inches.

C. Foliage: Compound 5 to 7 leaflets.
(1) *Size.*—Medium.
(2) *Quantity.*—Abundant.
(3) *Color.*—New foliage: Upper side — near 143A. Under side — near 146D. Old foliage: Upper side — near 137A. Under side — near to 138C.
(4) *Shape.*—Oval, pointed.
(5) *Texture.*—Upper side is semiglossy; under side is matte.
(6) *Edge.*—Serrate.
(7) *Serration.*—Ordinary.
(8) *Leaf stem.*—Color — near to 137C. Under side — near 144B.
(9) *Stipules.*—Medium, slightly bearded.
(10) *Resistance to disease.*—Blackspot — Average. Mildew — Average. Rust — Average.

D. Wood:
(1) *New wood.*—Color — near 148A. Bark — smooth.
(2) *Old wood.*—Color — near 137C. Bark — smooth.

E. Thorns:
(1) *Thorns.*—Quantity (main stalk) — ordinary. On laterals from stalk — few. Form — long, thin, straight, angled slightly downward. Length — medium. Color — near 180A. Position — irregular.
(2) *Prickles.*—None.

F. Winter hardness: Needs protection in severe climate.

I claim:

1. A new and distinct variety of rose plant of the miniature rose class, substantially as shown and described, characterized particularly by pink and cream blend flowers of excellent exhibition form which are long lasting on the plant and as cut flowers.

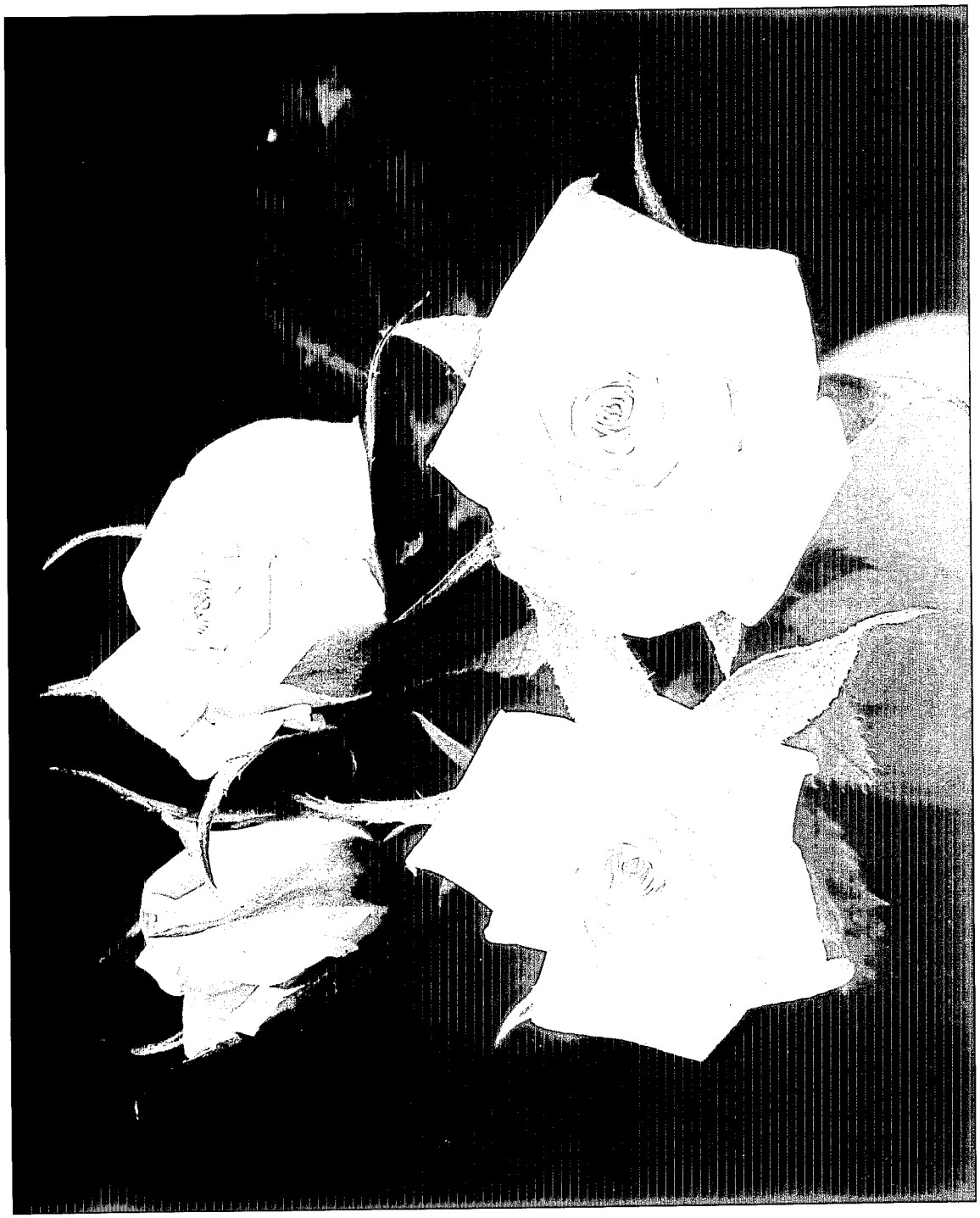

* * * * *